(12) United States Patent
Aunio et al.

(10) Patent No.: US 8,435,275 B2
(45) Date of Patent: May 7, 2013

(54) PORTABLE EAR LIGHT DEVICE

(75) Inventors: Antti Aunio, Oulu (FI); Markku Aunio, Oulu (FI)

(73) Assignee: Valkee Oy, Oulunsalo (FI)

( * ) Notice: Subject to any disclaimer, the term of this patent is extended or adjusted under 35 U.S.C. 154(b) by 27 days.

(21) Appl. No.: 13/075,397

(22) Filed: Mar. 30, 2011

(65) Prior Publication Data

US 2012/0253428 A1    Oct. 4, 2012

(51) Int. Cl.
*A61N 5/06*      (2006.01)

(52) U.S. Cl.
USPC .................................. 607/89; 607/9

(58) Field of Classification Search .................. 607/9, 89
See application file for complete search history.

(56) References Cited

U.S. PATENT DOCUMENTS

| | | | | |
|---|---|---|---|---|
| 7,883,535 B2* | 2/2011 | Cantin et al. | ..................... | 607/89 |
| 8,012,189 B1* | 9/2011 | Webb et al. | ..................... | 607/89 |
| 2006/0161227 A1* | 7/2006 | Walsh et al. | ..................... | 607/88 |
| 2010/0042188 A1* | 2/2010 | Nissila et al. | ..................... | 607/93 |
| 2011/0125222 A1* | 5/2011 | Perkins et al. | ..................... | 607/61 |

FOREIGN PATENT DOCUMENTS

| | | |
|---|---|---|
| JP | 2009034349 A | 2/2009 |
| WO | WO2008029001 A1 | 3/2008 |

* cited by examiner

*Primary Examiner* — Bill Thomson
*Assistant Examiner* — Jeffrey Lipitz
(74) *Attorney, Agent, or Firm* — Hoffmann & Baron, LLP

(57) ABSTRACT

A portable electronic ear light device comprising a support member and an optical radiation source resting on the support member and a light guide for directing optical radiation energy non-invasively at the user's intracranial nerve tissue via the outer auditory canal of the user of the portable electronic device to stimulate the user's intracranial nerve tissue. In the device, the support member is around the light guide at a distance from the radiation guide, thus providing an air gap around the radiation guide. In the device there is a sealing structure between the support member and the light guide for preventing the contamination of the light guide and the air gap.

10 Claims, 2 Drawing Sheets

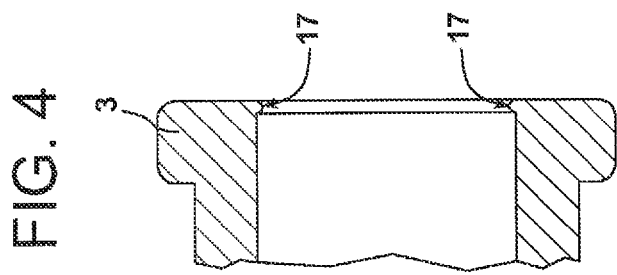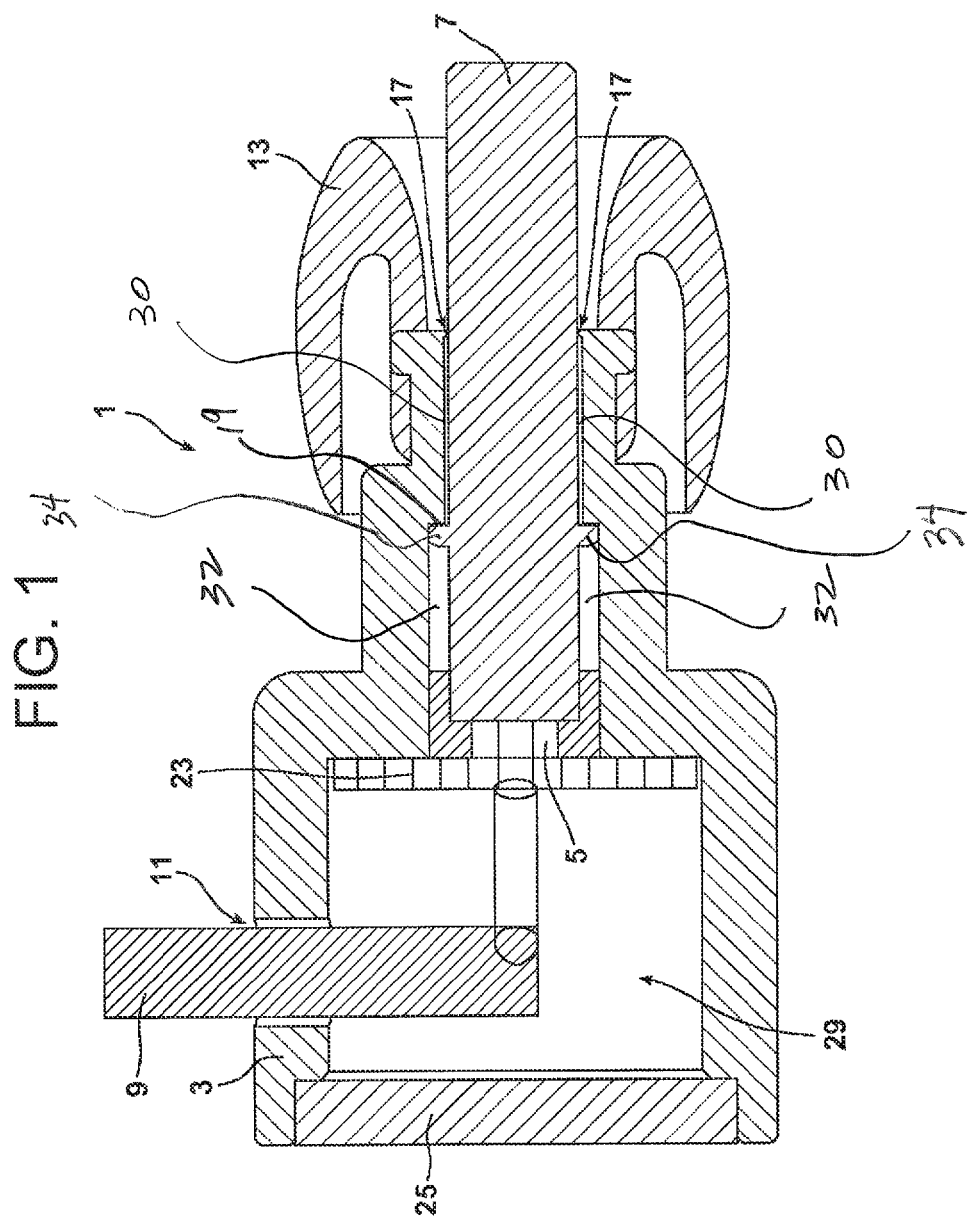

PORTABLE EAR LIGHT DEVICE

BACKGROUND

1. Field

The invention relates to a portable electronic ear light device.

2. Description of the Related Art

Human intracranial nerve tissue comprises regions that are stimulated by optical radiation directed at the regions. Stimulation may have a metabolic and/or nervous response, which appears as a change in alertness, circadian rhythm or contents of several hormones and neurotransmitters, for example. Presently known phenomena caused by a changed quantity of light include onset of mating behavior in wild animals and seasonal affective disorder SAD well-known in humans. Optical radiation may originate from nature, or optical radiation may have an artificial origin.

Artificial optical radiation must typically be used if natural light is not sufficient for producing a desired physiological effect. Artificial optical radiation may be generated by, for example, light therapy devices installed in homes or workplaces, for instance.

Disadvantages of light therapy devices include devices' big size, limited location, poor efficiency and disturbance to the surroundings. It is thus useful to consider alternative techniques for providing interaction between optical radiation and intracranial nerve tissue.

Portable earpiece type ear light devices are also known from publications WO2008/029001 and JP2009034349, for instance.

Known solutions are not necessarily optimal in terms of efficiency of luminosity propagation or tolerance of operating conditions.

SUMMARY

It is an object of the invention to implement a portable electronic device in such a manner that human intracranial nerve tissues can be stimulated easily and effectively. This is achieved by a portable electronic device, the device comprising a support member around a radiation guide at a distance from a light guide, thus providing an air gap around the light guide, and the device comprising a sealing structure between the support member and the light guide for preventing contamination of the light guide and the air gap.

Preferred embodiments of the invention are described in the dependent claims.

The invention is based on the idea that the structure of the device prevents the weakening of the refraction coefficient of light propagating in the light guide. The light guide is at a distance from the device body, and the seal prevents dirt from accessing the surface of the light guide.

BRIEF DESCRIPTION OF THE DRAWINGS

The invention will now be described in greater detail in connection with preferred embodiments and with reference to the accompanying drawings, in which FIG. 1 shows a cross section of an ear light device from the side, FIG. 4 shows an enlarged view of the tip of the support member with a seal protrusion.

DETAILED DESCRIPTION

Figure 2:
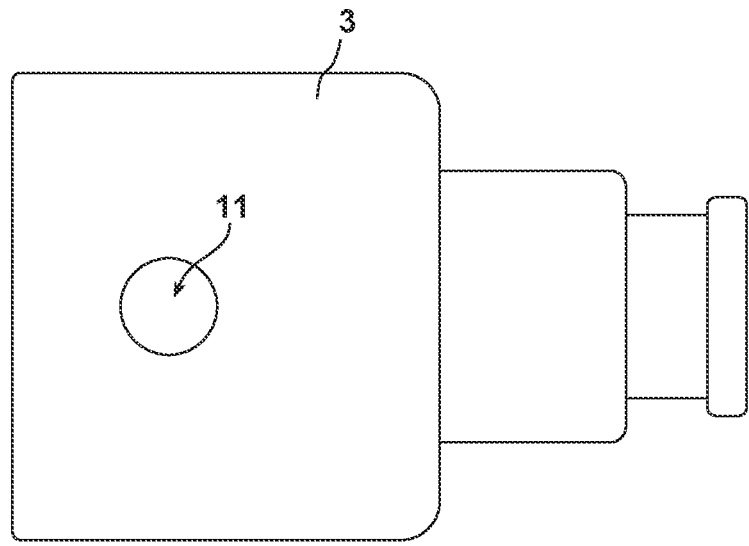
FIG. 2 shows a support member of the ear light device from the side.

A portable electronic ear light device 1 is a portable device the user carries without an external support means. In this case the external support refers, for example, to a support which supports the device by resting on the ground or other fixed structure. The user is a person capable of independently using a portable electronic device. The use comprises, for example, placing a portable electronic device on the body, switching the portable electronic device on and off, and performing operating settings of the portable electronic device.

In an embodiment, the portable electronic device is user-specific, in which case the person at whom the optical radiation is directed controls the portable electronic device himself via a user interface, for example.

A radiation member directs optical radiation at the user's outer auditory canal, which absorbs optical radiation and transmits the optical radiation energy to intracranial nerve tissue. Thus, the intracranial nerve tissue is subjected to a treatment that has a response in the intracranial nerve tissue. In this context, the terms "optical radiation" and "optical radiation energy" are equivalent concepts. Optical radiation typically comprises the wavelengths of infrared radiation, visible light and ultraviolet radiation.

Propagation of optical radiation energy is based on the optical propagation of radiation in tissue. When optical radiation energy propagates in tissue, part of it is converted into heat. In addition, the wavelength distribution of optical radiation typically changes due to absorption in tissue.

The power of optical radiation energy is selected in such a manner that the optical radiation energy reaches the intracranial nerve tissue.

In the described solution, optical radiation energy is directed at the intracranial nerve tissue non-invasively. In this case, the radiation member is outside the skin and does not penetrate into the user's tissue. In this context, also the inner surface of the outer auditory canal is defined as skin. Use of the outer auditory canal as an optical channel and use of the outer auditory canal walls as absorbers of optical radiation enable the use of low optical power in illuminating the intracranial nerve tissue.

The optical radiation energy is received in the radiation-sensitive intracranial nerve tissue, which is stimulated by the optical radiation energy 108. Stimulation typically appears as a nervous and/or hormonal response in the intracranial nerve tissue.

The intracranial nerve tissue responsive to optical radiation energy comprises, for instance, cerebrum, cerebellum, vestibular organs, auditory organs, olfactory organs, bulbus, and/or regions of autonomous regulation. The response may be based on a change in the concentration/content of melatonin hormone caused by the optical radiation, for example.

In an embodiment, the intracranial nerve tissue responsive to the optical radiation energy 108 comprises a pineal body, also known as a pineal gland.

In an embodiment, the intracranial nerve tissue responsive to optical radiation energy 108 comprises a retina, the ganglia cells of which may also sense light that comes from behind. Typically, the light perception of ganglia cells is independent of seeing and is not involved in seeing. Ganglia cells are particularly specialized in diffused light, and their photosensitive pigment is melanopsin protein. When subjected to light, ganglia cells signal the suprachiasmatic nucleus, which is responsible for the circadian rhythm.

In an embodiment, the intracranial nerve tissue responsive to optical radiation energy 108 comprises the suprachiasmatic nucleus (SCN), which regulates the pineal gland, which back-regulates the SCN by excreting melatonin.

It should be noted that the above-mentioned intracranial nerve tissues responsive to optical radiation energy are only examples. Part of the light also affects through other means than the neuroendocrinology of circadian rhythm. Intracranial nerve tissues, also in the cranial region, have several non-specific responses to optical radiation energy and the temperature increase caused by the optical radiation energy. Such responses include increase in the metabolism of tissues and changes in the immune response, for example.

With reference to FIGS. 1 to 4, a portable ear light device is thus described. The device comprises a support member 3 and an optical radiation source 5 resting on the support member and a light guide 7 for directing optical radiation energy non-invasively at the user's intracranial nerve tissue via the outer auditory canal of the user of the portable electronic device in order to stimulate the user's intracranial nerve tissue. The radiation source 5 is a LED, for example. The device also comprises a cable 9 for feeding current to the radiation source 5. The support member 3 comprises an opening 11 for the cable 9.

The support member 3 is a sleeve-like member acting as a casing, and a replaceable ear adapter 13 may be fixed at the tip of the support member 3.

In the device, the support member 3 is around the light guide 7 at a distance from the light guide 7, thus providing air gaps 30, 32 around the radiation or light guide 7. In the device there is also a sealing structure 17 between the support member and the radiation conductor to prevent the contamination of the light guide 7 and the air gaps 30, 32.

Figure 3:
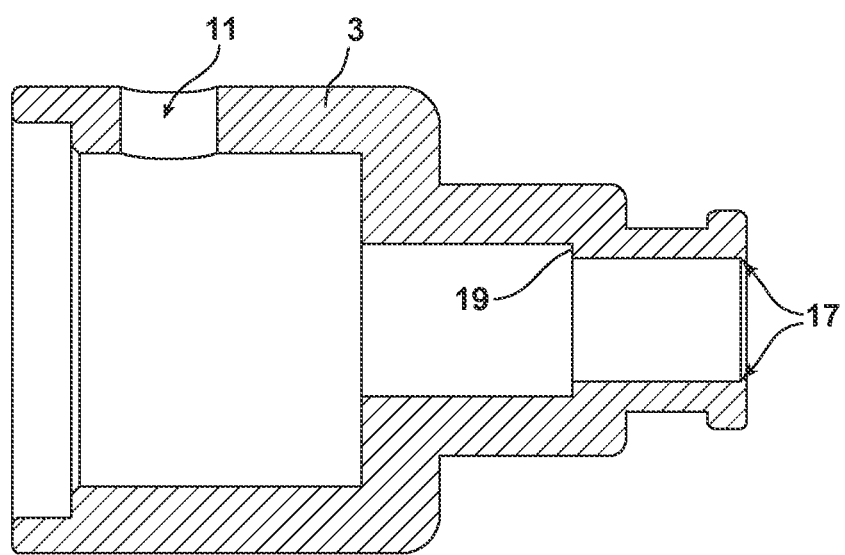
FIG. 3 shows a cross section of the structure according to FIG. 2.

FIGS. 1, 3 and 4 show that the sealing structure comprises a seal protrusion 17 protruding from the support member 3 and extending to contact the photoconductor or light guide 7. The seal protrusion 17 is a watertight sealing.

It is noted that, in the operating position of the device, the seal protrusion 17 protruding from the support member 3 is at that end of the air gap 30 surrounding the radiation guide 7 that is closest to the user.

With reference to FIGS. 1 and 3, between the light guide 7 and the support member 3 there is provided a support surface 19, 21 transverse to the longitudinal direction of the light guide and a protrusion 34 disposed on the light guide 7, which are arranged to position the light guide 7 in its place relative to the support member 3.

FIG. 1 shows that air gap 30 is surrounding the light guide 7 on the right side and air gap 32 is surrounding light guide on the left side of the support surface 19, 21, the air gap 30 on the right side being narrower in the vertical direction than the air gap 32 on the left side.

With reference to FIG. 1, the device comprises a circuit board 23 resting on the support member 3 of the device, and the optical radiation source, such as a LED, is located on the circuit board 23. The device also comprises a cover 25. At the assembly phase, the space between the circuit board 23 and the cover 25 is filled with a hot-setting adhesive 29, which acts as a clamp for the cable 9 and glues the cover 25 in its place.

The fact that the circuit board 23 rests on the support member 3 and/or the above-mentioned hot-setting adhesive prevent the contamination of the air gap and the light guide, i.e. serve as a seal structure when seen from the left in the figure. The same effect may also be accomplished by the support surface 19, 21, in other words, the seal structure comprises the support surface.

Although the invention is described above with reference to the example according to the accompanying drawings, it is clear that the invention is not restricted thereto, but may be modified in various ways within the scope of the accompanying claims.

What is claimed is:

1. A portable electronic ear light device comprising:
   a support member;
   an optical radiation source resting on the support member;
   a light guide to direct optical radiation energy non-invasively at intracranial nerve tissue of a user of the portable electronic device via an outer auditory canal of the user to stimulate the intracranial nerve tissue, the support member being disposed around the light guide at a distance from the light guide, thereby providing an air gap in contact with the light guide, the air gap is surrounding the light guide, the air gap being disposed between the light guide and the support member; and
   a sealing structure between the support member and the light guide to prevent contamination of the light guide and the air gap.

2. A portable electronic ear light device as claimed in claim 1, wherein the sealing structure comprises a seal protrusion protruding from the support member, the seal protrusion protruding from the support member and extending to contact the light guide, thereby sealing the air gap and preventing contamination of the air gap.

3. A portable electronic ear light device as claimed in claim 2, wherein, in an operating position of the device, the seal protrusion protruding from the support member is at that end of the air gap surrounding the light guide that is closest to the user.

4. A portable electronic ear light device as claimed in claim 1, wherein, between the light guide and the support member, there is provided a support surface transverse to a longitudinal direction of the light guide and arranged to position the light guide in place relative to the support member.

5. A portable electronic ear light device as claimed in claim 1, wherein, between the light guide and the support member, there is provided a support surface transverse to a longitudinal direction of the light guide, the sealing structure comprising the support surface.

6. A portable electronic device as claimed in claim 5, wherein, in an operating position of the device, the support surface of the sealing structure is at that end of the air gap surrounding the light guide that is farther away from the user.

7. A portable electronic device as claimed in claim 5, wherein the light guide comprises a protrusion arranged with the support surface to position the light guide in place relative to the support member.

8. A portable electronic device as claimed in claim 1, wherein the device comprises a circuit board resting on the support member, the radiation source being located on the circuit board.

9. A portable electronic device as claimed in claim 1, wherein the air gap disposed around that portion of the light guide closer to the user during use of the portable electronic device is narrower in a direction transverse to a longitudinal direction of the light guide than the air gap disposed around that portion of the light guide farther away from the user during use of the portable electronic device.

10. A portable electronic device as claimed in claim 1, wherein the air gap is disposed adjacent to the light guide.

* * * * *